US012773519B2

(12) United States Patent
Amans

(10) Patent No.: US 12,773,519 B2
(45) Date of Patent: Oct. 27, 2026

(54) SYSTEM AND METHOD FOR SOOTHING INFANTS

(71) Applicant: The Regents of the University of California, Oakland, CA (US)

(72) Inventor: Matthew Amans, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 630 days.

(21) Appl. No.: 18/261,693

(22) PCT Filed: Jan. 20, 2022

(86) PCT No.: PCT/US2022/013062
§ 371 (c)(1),
(2) Date: Jul. 17, 2023

(87) PCT Pub. No.: WO2022/159545
PCT Pub. Date: Jul. 28, 2022

(65) Prior Publication Data

US 2024/0293640 A1 Sep. 5, 2024

Related U.S. Application Data

(60) Provisional application No. 63/139,524, filed on Jan. 20, 2021.

(51) Int. Cl.
*A61M 21/02* (2006.01)
*A61M 21/00* (2006.01)

(52) U.S. Cl.
CPC ..... *A61M 21/02* (2013.01); *A61M 2021/0027* (2013.01); *A61M 2205/3375* (2013.01); *A61M 2205/505* (2013.01); *A61M 2230/63* (2013.01)

(58) Field of Classification Search
CPC .................... A61M 21/00–02; A61M 2240/00
See application file for complete search history.

(56) References Cited

U.S. PATENT DOCUMENTS

2013/0096368 A1 4/2013 Devroey
2014/0082839 A1 3/2014 Piombino
(Continued)

FOREIGN PATENT DOCUMENTS

CN 104800951 A * 7/2015
CN 109767751 A 5/2019
(Continued)

OTHER PUBLICATIONS

Extended Euroepan Search Report issued in corresponding application EP 22743143.4 dated Nov. 21, 2024 (7 pages).
(Continued)

*Primary Examiner* — Thaddeus B Cox
(74) *Attorney, Agent, or Firm* — Carter, DeLuca & Farrell LLP

(57) ABSTRACT

A system includes a wearable device disposed on a person, the wearable device has a plurality of sensors, each of which is configured to output a sound waveform in response to sounds generated by physiological activity of the person. The system also includes a processing device coupled to the plurality of sensors and configured to process and store the sound waveforms as sound files. The system also includes a sound output device coupled to the processing device. The sound output device is configured to output the sound files to mimic in utero sounds.

18 Claims, 2 Drawing Sheets

(56) References Cited

U.S. PATENT DOCUMENTS

| | | | | |
|---|---|---|---|---|
| 2014/0275742 | A1 | 9/2014 | Andrew | |
| 2015/0045608 | A1 | 2/2015 | Karp et al. | |
| 2015/0348389 | A1 | 12/2015 | Jang et al. | |
| 2017/0072162 | A1 | 3/2017 | Kim et al. | |
| 2020/0384239 | A1* | 12/2020 | Fornell | A61M 21/02 |
| 2022/0167930 | A1* | 6/2022 | Hannula | G06N 3/0499 |

FOREIGN PATENT DOCUMENTS

| | | | |
|---|---|---|---|
| CN | 111772422 | A | 10/2020 |
| JP | 2020092978 | A | 6/2020 |
| WO | 2020193842 | A1 | 10/2020 |

OTHER PUBLICATIONS

International Search Report and Written Opinion of the International Searching Authority issued in corresponding application PCT/US2022/013062 mailed May 5, 2022 (12 pages).

Office Action issued in corresponding Chinese Application No. 202280011053.6 dated Feb. 4, 2026, together with English language translation retrieved from the Global Dossier.

* cited by examiner

SYSTEM AND METHOD FOR SOOTHING INFANTS

CROSS REFERENCE TO RELATED APPLICATIONS

The present application is a U.S. National Stage Application filed under 35 U.S.C. § 371(a) of International Patent Application No. PCT/US2022/013062, filed on Jan. 20, 2022, which claims the benefit of and priority to U.S. Provisional Application No. 63/139,524, filed on Jan. 20, 2021. The entire disclosures of the foregoing applications are incorporated by reference herein.

BACKGROUND

It is well known that infants are calmed by their mother's sounds, such as breathing and voice. It is believed that the sounds indicate to the infant that their caregiver is present. The sound of the caregiver's heartbeat also calms infants when they are agitated and also puts them to sleep when they are tired. Thus, there is a need for a system and method to record, process, and/or amplify sounds generated by a caregiver and provide those to the infant to sooth them.

SUMMARY

The present disclosure provides a system and method for generating infant-soothing sounds. The system includes a sound output device, which may be a speaker located in proximity to the infant. The sound output device outputs real-time or prerecorded sounds, such as a person's, e.g., mother's, blood flow sounds, breathing sounds, heartbeat, digestion sounds, voice, and other sounds generated by physiological activity of the person, to sooth the infant by mimicking the sounds the infant experienced while in utero.

The sounds are recorded though a wearable device worn around a wrist or chest of the person. The wearable device includes a band having a plurality of sensors, which may be acoustic sensors, ultrasound transducers, or other transducers configured to pick up internal and external sounds generated by the person wearing the device. The wearable device is also in communication with a processing device, which may be a mobile phone, a tablet, or a remote computer (e.g., server), running a software application in communication with the wearable device and the sound output device. The processing device is configured to process one or more sound waveforms generated by the sensors of the wearable device. Processing of the waveforms may include mixing the waveforms to generate a single output waveform and/or muffling the sounds to mimic in utero sounds, isolating or separating different sound waveforms produced by different sources, or filtering the sound waves. Playback of the sounds may be done in real-time or using prerecorded sound files.

Furthermore, the sound output device is configured to detect whether the infant is calm or agitated by measuring the sound levels in the room via an embedded microphone. Upon a determination that the infant is agitated, which may be done by the sound output device and/or the processing device, or manually triggered by the caregiver, the sound output device automatically outputs either live or prerecorded sounds to sooth the infant. In addition, the level of agitation of the infant may be displayed on the wearable device to continuously provide feedback to the wearer as to the infant's state.

According to one embodiment of the present disclosure, a system for generating infant-soothing sounds is disclosed. The system includes a wearable device disposed on a person, the wearable device has a plurality of sensors, each of which is configured to output a sound waveform in response to sounds generated by physiological activity of the person. The system also includes a processing device coupled to the plurality of sensors and configured to process and store the sound waveforms as sound files. The system also includes a sound output device coupled to the processing device. The sound output device is configured to output the sound files to mimic in utero sounds.

Implementations of the above embodiment may include one or more of the following features. According to one aspect of the above embodiment, the sound output device may be configured to detect infant activity and the processing device may be configured to indicate a level of infant activity. The wearable device may include a band formed from an elastic material configured to induce arterial stenosis thereby increasing blood flow turbulence. The plurality of sensors includes at least one inner sensor disposed on an inner surface of the band and configured to measure sound generated by the blood flow turbulence. An alternate transducer to measure the sound of blood flow may employ ultrasound technology including Doppler effect-based ultrasound. The plurality of sensors may include at least one outer sensor disposed on an outer surface of the band and configured to measure external sounds. The sounds generated by physiological activity of the person include vascular sounds, respiratory sounds, digestion sounds, movement sounds, and miscellaneous sounds. The processing device is configured to categorize the sounds generated by physiological activity of the person and to store the sound files in corresponding storage banks. The processing device further includes a user input device configured to display a graphical user interface. The graphical user interface is configured to enable selection of at least one of the sound files for output through the sound output device. The sound output device includes a microphone and is configured to monitor a level of agitation of an infant based on sounds generated by the infant. The sound output device is further configured to output at least one of the sound files based on the level of agitation of the infant. The wearable device may be also configured to display the state of agitation of the infant to the wearer. The processing device is further configured to mix or separate the sound waveforms.

According to another embodiment of the present disclosure, a method for generating infant-soothing sounds is disclosed. The method includes placing a wearable device on a person, the wearable device includes a plurality of sensors. The method also includes generating a sound waveform at each sensor of the plurality of sensors in response to sounds generated by physiological activity of the person. The method also includes processing at a processing device the sound waveforms and storing the sound waveforms as sound files. The method also includes outputting the sound files to mimic in utero sounds at a sound output device coupled to the processing device.

Implementations of the above embodiment may include one or more of the following features. According to one aspect of the above embodiment the wearable device may include a band formed from an elastic material configured to induce arterial stenosis thereby increasing blood flow turbulence. The plurality of sensors includes at least one inner sensor disposed on an inner surface of the band and configured to measure sound generated by the blood flow turbulence. The plurality of sensors includes at least one outer sensor disposed on an outer surface of the band and configured to measure external sounds. The sounds generated by physiological activity of the person includes vascular sounds, respiratory sounds, digestion sounds, movement sounds, and miscellaneous sounds. The method may also include categorizing the sounds generated by physiological activity of the person; and storing the sound files in corresponding storage banks. The method may further include monitoring a level of agitation of an infant based on sounds generated by the infant through a microphone disposed in the sound output device and outputting at least one of the sound files based on the level of agitation of the infant.

BRIEF DESCRIPTION OF THE DRAWINGS

Embodiments of the present disclosure are described herein with reference to the accompanying drawings, wherein.

DETAILED DESCRIPTION

Figure 1:
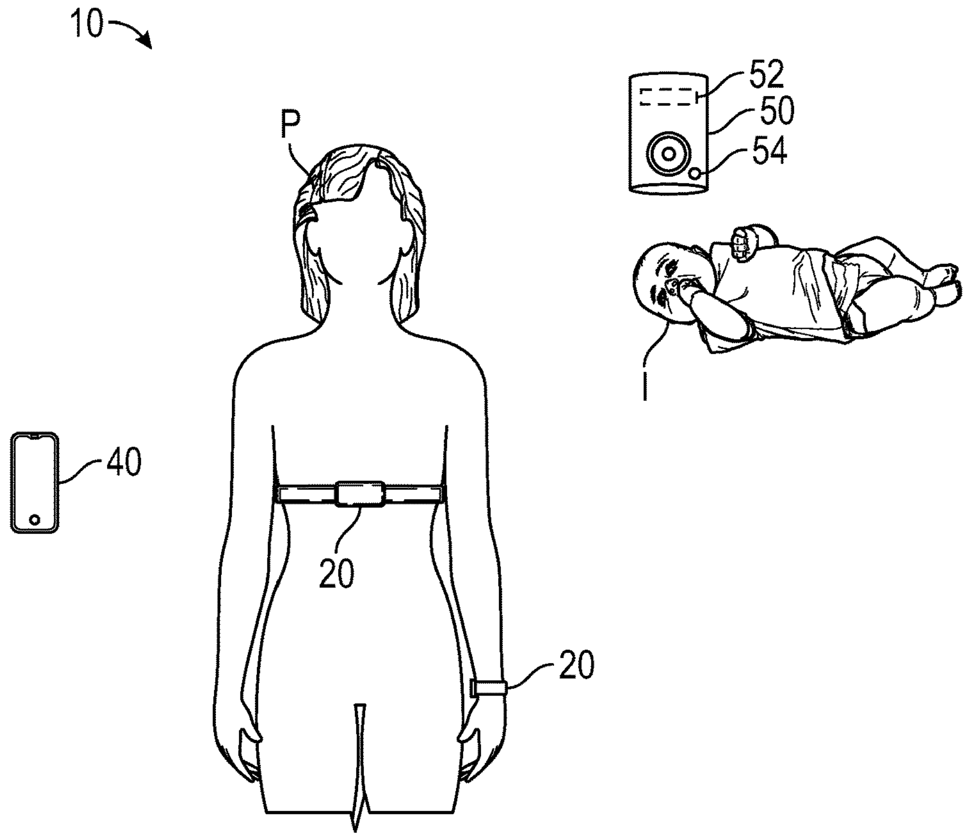
FIG. 1 is a schematic diagram of a system for generating infant-soothing sounds according to one embodiment the present disclosure.

Embodiments of the present disclosure are described in detail with reference to the drawings, in which like reference numerals designate identical or corresponding elements in each of the several views. FIG. 1 shows a system 10 for generating infant-soothing sounds to calm and sooth an infant "I". The system 10 includes one or more wearable devices 20 having one or more sensors that are connected to a processing device 30 (FIG. 2), which in turn is connected to a sound output device 50. In embodiments, the processing device 30 may be a computing device 40, i.e., a tablet or a mobile phone. In further embodiments, the computing device 40 may be used in conjunction with the processing device 30.

Figure 2:
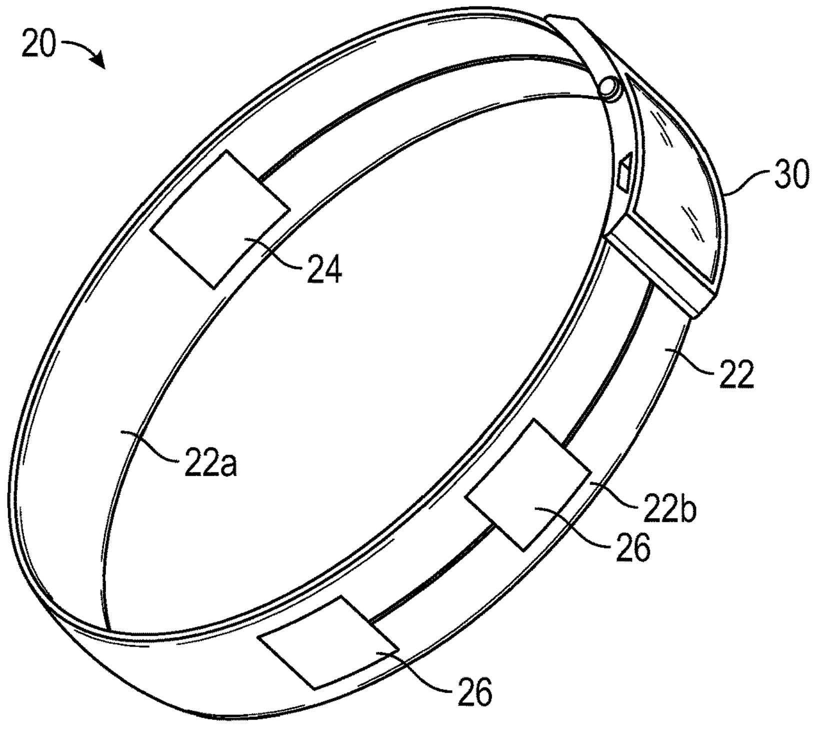
FIG. 2 is a perspective view of a wearable device for receiving sounds according to one embodiment the present disclosure.

With reference to FIGS. 1 and 2, the wearable device 20 may be worn at one or more locations around the body or a limb of a person "P", such as a wrist, ankle, chest, etc. The wearable device 20 may be attached to the person "P" using a band 22 or an adhesive bandage (not shown), such that the wearable device 20 is in physical contact with the person "P" allowing for measurement of sounds generated by the person "P", e.g., mother.

When the wearable device 20 is worn around the wrist, the band 22 may be formed from an elastic material, such as silicone, rubber, combinations thereof, or any other suitable stretchable elastomer. The band 22 is fitted about the wrist to induce arterial stenosis, thereby generating blood flow turbulence to enhance sound generation associated with the blood flow. When the wearable device 20 is worn around chest, any suitable strap may be used, such as an adjustable and/or an elastic strap. The band 22 may be formed as a single strip. In embodiments, the band 22 may be formed from one or more strips or filaments woven in any suitable pattern.

The wearable device 20 includes one or more inner sensors 24 disposed an inner surface 22*a* (i.e., surface directly in contact with the person "P") of the band 22. The inner sensor 24 is configured to measure sounds generated within the person "P." The inner sensor 24 may be a microphone or any other type of acoustic transducer configured to measure sound, such as a flexible membrane transducer, a micro-electromechanical systems (MEMS) microphone, an electret diaphragm microphone, or any other microphone. When the wearable device 20 is worn around the wrist, the inner sensor 24 picks up sounds generated by the blood flow, which is accentuated by the compression of the band 22. When the wearable device 20 is worn around chest, the inner sensor 24 picks up sounds generated by the heard, digestive system, respiratory system of the person "P."

In embodiments, the inner sensor 24 may be a heartrate monitor such as an electrocardiography ("ECG") sensor. The ECG sensor is configured to measure electrical activity of the heart and is disposed on the chest of the person "P". The inner sensor 24 may also be a photoplethysmography-based sensor which uses optical sensors to detect volume of blood flow. Since the optical sensor measures blood flow, the inner sensor 24 may be placed at any suitable location having sufficient blood flow.

According to another embodiment, the inner sensor 24, i.e., when the wearable device 20 is worn around the wrist, may be an ultrasound device configured to measure the blood flow and in the absence of turbulence present the information as a sound waveform using Doppler effect or any other suitable technique. The inner sensor 24 may also be any other suitable transducer, such as an optical transducer, capable of measuring normal blood flow and transmitting blood flow sounds in the absence of turbulence.

The wearable device 20 also includes one or more outer sensors 26 disposed on an outer surface 22*b* of the band 22. The outer sensor 26 may be the same type of sensor as the inner sensor 24. The outer sensor 26 is configured to pick up sounds generated by the person "P" including, but not limited to, vocal, movement, respiratory, and other sounds.

The sensors 24 and 26 are coupled to a processing device 30, which is shown as being attached to the band 22. In embodiments, the processing device 30 may be a standalone device that is separated from the wearable device 20. The sensors 24 and 26 may be coupled to the processing device 30 either through a wired or a wireless communication interface. The sensors 24 and 26 output sound waveform signals corresponding to various sounds generated by the person "P," which are then processed by the processing device 30. In further embodiments, the sensors 24 and 26 may be incorporated into a housing the processing device 30—with the inner sensor 24 disposed on an inner surface of the processing device 30 and the outer sensor 26 disposed on an outer surface of the processing device 30.

Figure 3:
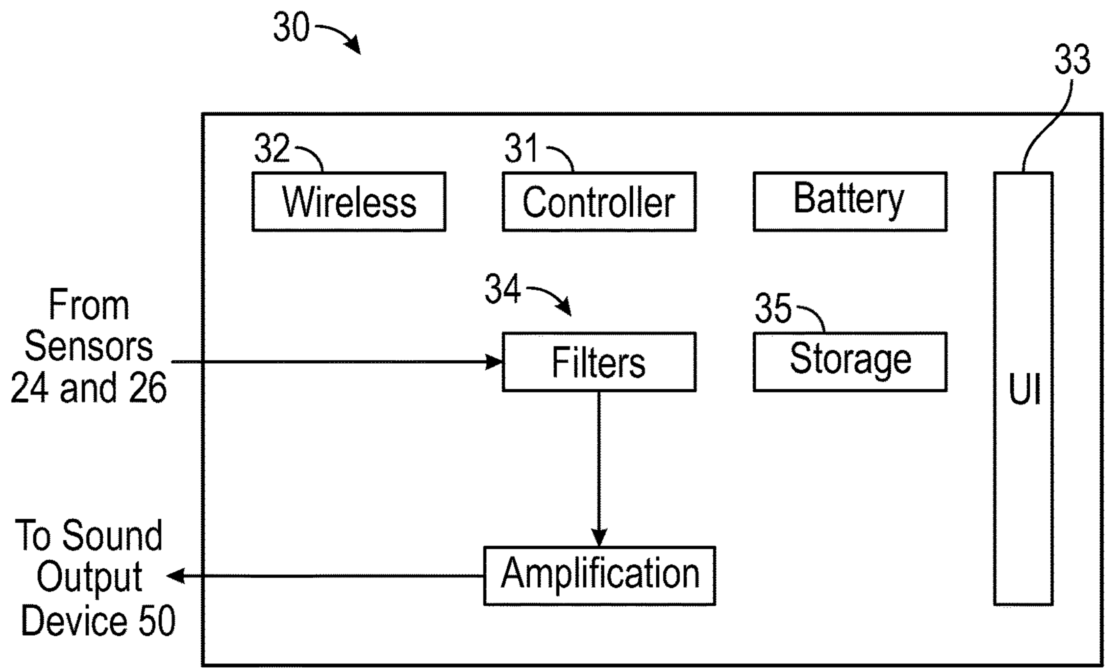
FIG. 3 is a schematic diagram of a processing device of the system of FIG. 2 according to one embodiment of the present disclosure.

With reference to FIG. 3, the processing device 30 includes a controller 31, which may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted by any logic processor (e.g., control circuit) adapted to execute algorithms, calculations, and/or set of instructions described herein.

The system 10 may also include the computing device 40 (FIG. 1), such as a handheld device having a touchscreen and an application for communicating with the processing device 30 thereby replicating the functionality of the user input device 33 and/or other functions of the processing device 30 described herein. In embodiments, the computing device 40 may communicate directly with the wearable device 20, obviating the need for the processing device 30. It is envisioned that various computing environments and architectures may be implemented to provide for measuring, recording, and processing of sounds generated by the person "P" for real-time or subsequent playback on the sound output device 50.

The controller 31 may also include a memory, which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The controller 31 and the memory device may be any standard processor and memory component known in the art.

The processing device 30 further includes a wireless interface 32, which may include an antenna and any other suitable transceiver circuitry configured to communicate with external devices (e.g., sensors 24 and 26) using wireless communication protocols. Wireless communication may be achieved via one or more wireless configurations, e.g., radio frequency, optical, Wi-Fi, ANT+, BLUETOOTH®, (an open wireless protocol for exchanging data over short distances, using short length radio waves, from fixed and mobile devices, creating personal area networks (PANs), ZIGBEE® (a specification for a suite of high level communication protocols using small, low-power digital radios based on the IEEE 802.15.4-2003 standard for wireless personal area networks (WPANs)), and the like. The processing device 30 may also include a user input device 33, having a display, i.e., a touchscreen and/or one or more buttons, which allows for the user to control operating of the processing device 30.

The processing device 30 further includes a waveform processing circuit 34, which may include discrete components or may be configured as a single circuit. The waveform processing circuits 34 may be analog or digital, which may be embodied in the controller 31. The sound waveform signal may be digitized by using any suitable method, such as Fourier transform algorithms. The processing device 30 may include any suitable electronic components, such as analog-to-digital (A/D) converters to digitize the sound waveform signal.

One of the waveform processing circuits 34 may be a filtering circuit configured to block and/or pass certain frequencies. The filtering circuit may include one or more of the following filters: high pass, low pass, band pass, notch filters and/or digital equivalents thereof. Thus, the filtering circuit may be configured to adjust the pitch of the sound waveforms. In further embodiments, the filtering circuits may modify the waveform to muffle the sound. The filtered sound waveform signal may also be amplified through an amplifier. The amplitude may be adjusted by the user through the user input device 33. The sound waveform may be divided into component waveforms according to sound source generation potentially using deconvolution and matching waveforms to preset banks of waveforms using machine learning.

The processing device 30 also includes storage 35 for storing recorded sound waveforms as sound files for subsequent playback through the sound output device 50. The processing device 30 may operate either in real time by outputting sound waveforms through the sound output device 50 or outputting prerecorded sound waveforms. The storage 35 may include a database of various sounds recorded by the sensors 24 and 26. Recorded sounds may be categorized based on the source of the sound. Thus, sounds recorded by the inner sensors 24 of the wearable device 20 disposed on the wrist provide vascular (i.e., blood flow) sounds. Similarly, the inner sensors 24 of the wearable device 20 disposed on the chest provide vascular (i.e., heartbeat), respiratory, and digestion sounds. The outer sensors 24 and 26 provide vocal and movement sounds as well as respiratory sounds. Each of these sounds are stored in corresponding storage banks that are accessible by the database. In particular, storage banks may be categorized by the type of sound, such as including, but not limited to, a vascular bank, a vocal bank, a respiratory bank, a digestion bank, a movement bank, and a miscellaneous bank.

In addition to storing the sound waveforms based on the source sensor, the person "P" may play back the sounds and manually sort the recorded sound using the user input device 33. In further embodiments, sortation and identification of the sounds may be done automatically by the processing device 30 and/or the computing device 40 using machine learning. It is envisioned that there may be an ongoing training of the identification process to automatically identify the sound using artificial intelligence.

The terms "artificial intelligence," "data models," or "machine learning" may include, but are not limited to, neural networks, convolutional neural networks (CNN), recurrent neural networks (RNN), generative adversarial networks (GAN), Bayesian Regression, Naive Bayes, nearest neighbors, least squares, means, and support vector regression, among other data science and artificial science techniques.

A neural network may be used to train the processing device 30 and/or the computing device 40. In various embodiments, the neural network may include a temporal convolutional network, with one or more fully connected layers, or a feed forward network. In various embodiments, training of the neural network may happen on a separate system, e.g., graphic processor unit ("GPU") workstations, high performing computer clusters, etc., and the trained algorithm would then be deployed on the processing device 30. In further embodiments, training of the neural networks may happen locally, e.g., on the processing device 30 and/or the computing device 40. After training, the processing device 30 may include a software application that is executable by the controller 31 to identify and sort various recorded sounds into corresponding storage banks.

Figure 4:
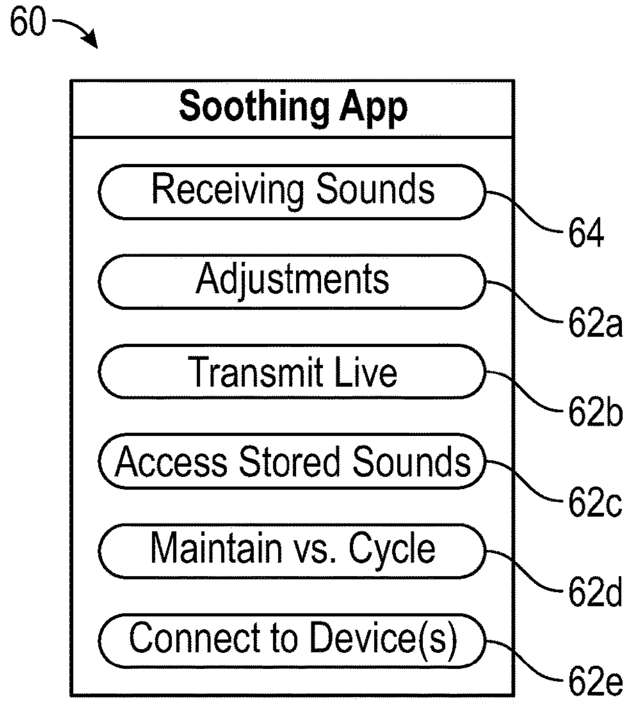
FIG. 4 is a schematic diagram of a graphical user interface of the processing device of FIG. 3 according to one embodiment the present disclosure.

With reference to FIG. 4, an exemplary graphical user interface ("GUI") 60 is shown on a display of the user input device 33. The GUI 60 may include a plurality of buttons **62*a-e* providing a user with options for controlling the system 10 and indicator 64 providing status of the system 10. The indicator 64 may use color and other indicia to provide status for each of the components of the system 10, namely, the wearable device 20, the processing device 30, the computing device 40, and the sound output device 50. The button 62*a* may be used to adjust operation of the system 10, i.e., enabling specific sensors 24 and 26, setting location of the sound output device 50, etc. The button 62*b* allows the user to configure the system 10 for real-time transmission of sounds recorded by the sensors 24 and 26 to the sound output device 50. The button 62*c* allows the user to access the storage banks having prerecorded sounds and select one or more of the sounds for playback through the sound output device 50. The button 62*d* is used to select between playback types. Playback type may include a cycling mode, in which the sound output device 50 cycles through different sound banks or individual sounds within a specific sound bank. Another mode may be a continuous mode in which one or more sounds are looped continuously until ended. The button 62***e* may be used to access a configuration screen for connecting to other devices of the system 10, such as the wearable device 20 and the sound output device 50.

The sound output device 50 may be any suitable speaker, e.g., a baby monitor, disposed near or worn by the infant "I." The sound output device 50 may be positioned in the room or on the crib. In embodiments, the sound output device 50 may be sown in, or otherwise embedded in a toy, or clothing worn by the infant "I." The sound output device 50 is configured to output sounds recorded by the wearable device 20 and transmitted by the processing device 30 and/or the computing device 40.

The sound output device 50 may be any wireless speaker, e.g., baby monitor, configured to communicate with the processing device 30 and/or the computing device 40. The sound output device 50 may also include a storage device 52 and a microphone 54. The storage device 52 may store the prerecorded sound waveforms from the processing device 30. In embodiments, the storage device 52 may be a cloud-based storage service that is accessible by the system 10. The sound output device 50 is configured to monitor a level of agitation of the infant "I." Playback may also be initiated by the person "P" or in response to detection of agitation or other events by the sound output device 50 via the microphone 54. More specifically, the sound output device 50 outputs live or prerecorded sounds, such as mother's blood flow sounds, breathing sounds, heartbeat, digestion sounds, voice, and other sounds generated by physiological activity of the person "P" body to sooth the infant "I" by mimicking in utero sounds. These sounds sooth the infant "I" since they have grown accustomed to such sounds while in utero.

The microphone 54 is configured to monitor any activity by the infant "I" for automatic activation of the sound output device 50. The sound output device 50 may include a controller configured to determine whether a detected sound corresponds to movement or agitation, e.g., crying, grunts, etc., of the infant "I" or the sound output device 50 may transmit the recorded sound to the processing device 30 and/or the computing device 40 to make this determination. Once it is determined that the infant "I" is agitated, the processing device 30 and/or the computing device 40 transmit or otherwise instruct the sound output device 50 to output a soothing sound to attempt to calm the infant "I." The sound output is based on the selections made by the person "P" through the GUI 60, such as which sounds to output and the output mode, i.e., cycle vs. maintain. More specifically, the sound output device 50 may be instructed to output one of the sounds or a plurality of the sound waveforms simultaneously. In embodiments, the processing device 30 and/or the computing device 40 may overlay and/or mix multiple waveforms, namely, sounds from multiple storage banks.

In addition, the processing device 30 and/or the computing device 40 may also output sound level or other indicator of infant activity, which may be displayed as a decibel bar on the GUI 60. The sound output device 50 may include a camera configured to detect infant motion. Thus, sound and/or motion detection may be used to determine a level of infant activity. In further embodiments, the processing device 30 and/or the computing device 40 may include a haptic device configured to vibrate the device 30 or 40 in response to a notification of infant activity. The wireless communication capabilities of the processing device 30 and/or the computing device 40 allow for using these devices from any distance relative to the infant.

During initial setup of the system 10, the person "P" attaches one or more wearable devices 20 to suitable locations on the body, i.e., chest and/or wrist. The person "P" also pairs the sound output device 50 to the processing device 30 and/or the computing device 40. In embodiments, where the computing device 40 is part of the system 10, the processing device 30 may be also paired to the computing device 40 to enable communication with the application running on the computing device 40. Once the initial setup is completed, the processing device 30 is configured to output the sounds based on the options selected through the GUI 60 as described above.

Figure 5:
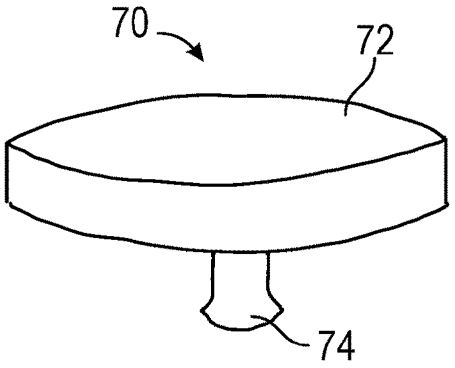
FIG. 5 is a perspective view of a wearable transducer assembly according to one embodiment the present disclosure.

With reference to FIG. 5, the system 10 may also include additional devices configured to couple to the processing device 20 and/or computing device 16. In particular, the system 10 may include a transducer assembly 70 having a housing 72, which may enclose the sensor 24 as well as other components of the processing device 20, such as a driver circuit, a transmitter, etc. The transducer assembly 70 may include a post 74 or other attachment means configured to secure the transducer assembly 70 to a band worn around the patient's wrist (e.g., watchband of an Apple Watch®). The transducer assembly 70 may be positioned on the underside of the watchband, such that the transducer assembly 70 is positioned over the artery.

It will be appreciated that of the above-disclosed and other features and functions, or alternatives thereof, may be desirably combined into many other different systems or applications. Various presently unforeseen or unanticipated alternatives, modifications, variations or improvements may be subsequently made by those skilled in the art which are also intended to be encompassed by the following claims. Unless specifically recited in a claim, steps or components of claims should not be implied or imported from the specification or any other claims as to any particular order, number, position, size, shape, angle, or material.

What is claimed is:

1. A system for generating infant-soothing sounds, the system comprising:

- a wearable device configured to be disposed on a person, the wearable device including:
  - a band formed from an elastic material configured to induce arterial stenosis thereby increasing blood flow turbulence; and
  - a plurality of sensors, each of which is configured to output a sound waveform in response to sounds generated by physiological activity of the person;
- a processing device coupled to the plurality of sensors and configured to process and store the sound waveforms as sound files; and
- a sound output device coupled to the processing device, the sound output device configured to output the sound files to mimic in utero sounds.

2. The system according to claim 1, wherein the sound output device is configured to detect infant activity and the processing device is configured to indicate a level of infant activity.

3. The system according to claim 1, wherein the plurality of sensors includes at least one inner sensor disposed on an inner surface of the band and configured to measure sound generated by the blood flow turbulence, and the at least one inner sensor is at least one of an acoustic sensor, an ultrasound sensor, or an optical sensor.

4. The system according to claim 1, wherein the plurality of sensors includes at least one outer sensor disposed on an outer surface of the band and configured to measure external sounds, and the at least one outer sensor is an acoustic sensor.

5. The system according to claim 1, wherein the sounds generated by physiological activity of the person include at least one of vascular sounds, respiratory sounds, digestion sounds, or movement sounds.

6. The system according to claim 5, wherein the processing device is configured to categorize the sounds generated by physiological activity of the person and to store the sound files in corresponding storage banks.

7. The system according to claim 6, wherein the processing device further includes a user input device configured to display a graphical user interface.

8. The system according to claim 7, wherein the graphical user interface is configured to enable selection of at least one of the sound files for output through the sound output device.

9. The system according to claim 1, wherein the sound output device includes a microphone and is configured to monitor a level of agitation of an infant based on sounds generated by the infant.

10. The system according to claim 9, wherein the sound output device is further configured to output at least one of the sound files based on the level of agitation of the infant.

11. The system according to claim 1, wherein the processing device is further configured to mix the sound waveforms.

12. A method for generating infant-soothing sounds, the method comprising:

placing a wearable device on a person, the wearable device including:

a band formed from an elastic material configured to induce arterial stenosis thereby increasing blood flow turbulence; and a plurality of sensors;

generating a sound waveform at each sensor of the plurality of sensors in response to sounds generated by physiological activity of the person;

processing at a processing device the sound waveforms and storing the sound waveforms as sound files; and outputting the sound files to mimic in utero sounds at a sound output device coupled to the processing device.

13. The method according to claim 12, wherein the plurality of sensors includes at least one inner sensor disposed on an inner surface of the band and configured to measure sound generated by the blood flow turbulence, and the at least one inner sensor is at least one of an acoustic sensor, an ultrasound sensor, or an optical sensor.

14. The method according to claim 12, wherein the plurality of sensors includes at least one outer sensor disposed on an outer surface of the band and configured to measure external sounds, and the at least one outer sensor is an acoustic sensor.

15. The method according to claim 12, wherein the sounds generated by physiological activity of the person include at least one of vascular sounds, respiratory sounds, digestion sounds, or movement sounds.

16. The method according to claim 15, further comprising:

categorizing the sounds generated by physiological activity of the person; and storing the sound files in corresponding storage banks.

17. The method according to claim 12, further comprising:

monitoring a level of agitation of an infant based on sounds generated by the infant through a microphone disposed in the sound output device.

18. The method according to claim 17, further comprising:

outputting at least one of the sound files based on the level of agitation of the infant.

* * * * *